(12) United States Patent
Eggink

(10) Patent No.: US 7,229,786 B2
(45) Date of Patent: Jun. 12, 2007

(54) METHOD OF PRODUCING PURIFIED CAROTENOID COMPOUNDS

(75) Inventor: Laura Eggink, Scottsdale, AZ (US)

(73) Assignee: Arizona Board of Regents, Phoenix, AZ (US)

( * ) Notice: Subject to any disclaimer, the term of this patent is extended or adjusted under 35 U.S.C. 154(b) by 921 days.

(21) Appl. No.: 10/169,117

(22) PCT Filed: Dec. 28, 2000

(86) PCT No.: PCT/US00/35503

§ 371 (c)(1),
(2), (4) Date: Jun. 25, 2002

(87) PCT Pub. No.: WO01/51648

PCT Pub. Date: Jul. 19, 2001

(65) Prior Publication Data
US 2004/0225167 A1    Nov. 11, 2004

Related U.S. Application Data

(60) Provisional application No. 60/175,187, filed on Jan. 10, 2000.

(51) Int. Cl.
*C12P 23/00* (2006.01)
(52) U.S. Cl. .................... 435/67; 435/257.1; 435/257.6
(58) Field of Classification Search .................. 435/67, 435/257.6
See application file for complete search history.

(56) References Cited

U.S. PATENT DOCUMENTS

| 4,871,551 A | 10/1989 | Spencer |
| 5,360,730 A | 11/1994 | Orndorff et al. |
| 5,382,714 A * | 1/1995 | Khachik ..................... 568/834 |

FOREIGN PATENT DOCUMENTS

| JP | 224029 | 8/1995 |
| WO | WO 99/48487 | 9/1999 |

OTHER PUBLICATIONS

XP002169633: Database WPI, Secton Ch., Week 199542, Derwnt Publications Ltd., Loindon, GB; Class B05, AN 1995-325524, and JP 07 224029 A (Sogo Biyo Ikagaku Kenekyusho KK), Aug. 22, 1995 abstract.
XP001002746: Park Hyoungshin et al.: "Transfer of proteins from the chloroplast to vacuoles in Chlamydomonas reinhardtii (Chlorophyta): A pathway for degradation." Journal of Phycology, vol. 35, No. 3, Jun. 1999, pp. 528-538, ISSN: 0022-3646.

* cited by examiner

*Primary Examiner*—Herbert J. Lilling
(74) *Attorney, Agent, or Firm*—Snell & Wilmer L.L.P.

(57) ABSTRACT

A method of producing a carotenoid in solid form includes culturing a strain of Chlorophyta algae cells in a minimal inorganic medium and separating the algae comprising a solid form of carotenoid. In one embodiment f the invention, the strain of Chlorophyta algae cells includes a strain f *Chlamydomonas* algae cells.

12 Claims, 3 Drawing Sheets

METHOD OF PRODUCING PURIFIED CAROTENOID COMPOUNDS

This application is a 371 of PCT/US00/35503 Dec. 28, 2000 which is a CON of No. 60/175,187 Jan. 10, 2000.

STATEMENT OF GOVERNMENT INTEREST

Financial Assistance for this project was provided by the U.S. Government through the National Science Foundation under Grant No. DGE-9553456 and through the National Aeronautics and Space Administration (NASA) under Grant No. NAG-W547. The United States Government may own certain rights to this invention.

FIELD OF INVENTION

The invention relates to methods for preparing carotenoids, and in particular, to the production of carotenoids using various strains of algae.

BACKGROUND OF THE INVENTION

It is now generally recognized in medical circles that antioxidants play an important role in nutrition and in the prevention of certain diseases, such as macular degeneration of the eye. Accordingly, it is now routinely recommended that individuals consume a "recommended daily allowance" of antioxidants to maintain good health.

Among the important antioxidants are the carotenoids, of which the most commonly known is beta-carotene. Other common carotenoids are the oxygenated form of beta-carotene, known as lutein, and another oxygenated carotenoid found in relatively low amounts in green plants and algae, zeaxanthin.

While the carotenoids are known to have important health effects, these compounds are currently manufactured by expensive processes requiring extraction of the compounds from a natural source, and subsequent purification. As a result, for example, lutein, which is an abundant plant and algal carotenoid, is currently sold for about $50,000 per gram. Zeaxanthin, produced from certain cyanobacteria, has a market price of approximately $100,000 per gram. These prices do not reflect scarcity, but rather the high cost of manufacture.

There is a great need for an inexpensive source of carotenoids to promote human health, such as the treatment of hives and other dermatoses, and prevent certain types of eye disorders, such as macular degeneration.

SUMMARY OF THE INVENTION

This summary of invention section is intended to introduce the reader to aspects of the invention and is not a complete description of the invention. Particular aspects of the invention are pointed out in other sections hereinbelow, and the invention is set forth in the appended claims which alone demarcate its scope.

The invention provides a unique method of preparing a carotenoid, zeaxanthin, through use of an alga. In particular, in one embodiment of the invention a Chlorophyta alga is cultured in a medium in the presence of light, and then harvested. The harvested cells are separated, for example, by centrifugation, and contain zeaxanthin and lutein, among other components, in a solid product. The carotenoids are present in a sufficient concentration in the solid for therapeutic or prophylactic administration to humans, or may be further purified to increase carotenoid concentration.

BRIEF DESCRIPTION OF THE DRAWINGS

The following drawings are illustrative of embodiments of the invention and therefore do not limit the scope of the invention, but are presented to assist in providing a proper understanding of the invention. The drawings are not to scale, and are intended for use in conjunction with the explanations in the following detailed description section.

DETAILED DESCRIPTION OF THE INVENTION

This section describes aspects of the invention, and points out certain preferred embodiments of these aspects. This section is not intended to be exhaustive, but rather to inform and teach the person of skill in the art who will come to appreciate more fully other aspects, equivalents, and possibilities presented by the invention, and hence the scope of the invention as set forth in the claims which alone limit its scope.

In accordance with an embodiment of the invention, a strain of Chlorophyta green algae is cultured under mild conditions in a minimal inorganic medium to produce cells that, upon harvesting, contain a relatively high concentration of carotenoids. The Chlorophyta algae may include the genus Chlamydomonas, Dunaliella, or any other suitable Chlorophyta algae. The medium may be formed of the following: 7.5 mM sodium acetate or sodium bicarbonate, 1.0 mM sodium citrate, 3.0 mM $K_2PO_4$, 7.0 mM $KH_2PO_4$, 7.5 mM $NH_4Cl$, 0.1 mM $CaCl_2$, 1.0 mM MgSO4, 0.01 mM $FeCl_3$ supplemented with 1 ml/l trace metals in the concentration of(mg/100 ml) $H_3BO_3$, 100; $ZnSO_4.7H_2O$, 100; $MnSO_4.4H_2O$, 40; $CoCl_2.6H_2O$, 20; $Na_2MoO_4.2H_2O$, 20; $CuSO_4.5H_2O$, 6. This description of the medium is not to be limiting and it will be appreciated that any suitable medium for growing Chlorophyta may be used. The Chlorophyta algae cells are grown in a temperature range of from approximately 25° C. to about 35° C. for a period of 3 to about 14 days. A detergent-insoluble pellet, for example, a Triton-X 100-insoluble pellet, prepared from these cells contains most of the zeaxanthin. The detergent insoluble pellet containing the algae cells may be extracted by suspending the pellet in a phosphate buffer, a Tris-HCL solution or any suitable suspending medium containing 1.0% (W/V) detergent, and sonicating and cetrifuging the mixture. The pellet may then be prepared for use as a nutritional supplement by, for example, drying it and/or encapsulating. Alternatively, it may be subjected to heat to isolate the carotenoids.

In this example approximately 2 μg/mg of oxygenated carotenoid may be isolated with the pellet (granule) preparation. This procedure could apply to any carotenoid selected by spontaneous or engineered mutation to be synthesized in Chlorophyta. For example, a strain producing only zeaxanthin would yield a granular product containing zeaxanthin as the sole oxygenated carotenoid. Some carotenoid mutations may generate light sensitive strains of algae; however, due to the flexibility of Chlorophyta to growth conditions, the strain may be grown in the dark as long as a suitable carbon source such as acetate or glucose is provided. Stress, such as nutrient depravation, may also stimulate synthesis and transfer of selected carotenoids to the granule.

EXAMPLE

Figure 2:
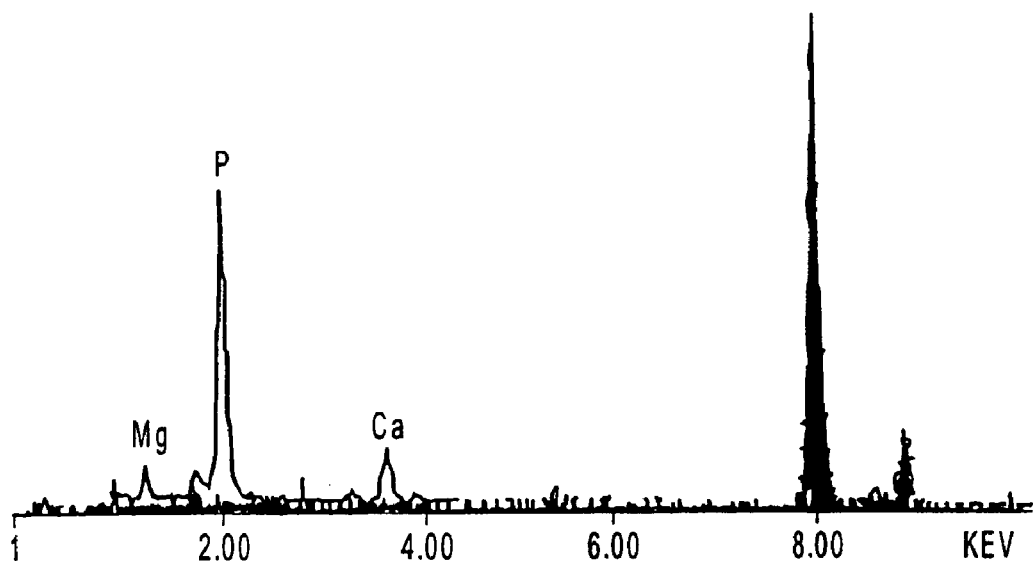
FIG. 2 is an EDAX analysis of the pellet of FIG. 1, showing the predominant inorganic component is phosphate, with divalent calcium and magnesium cations.
Figure 3:
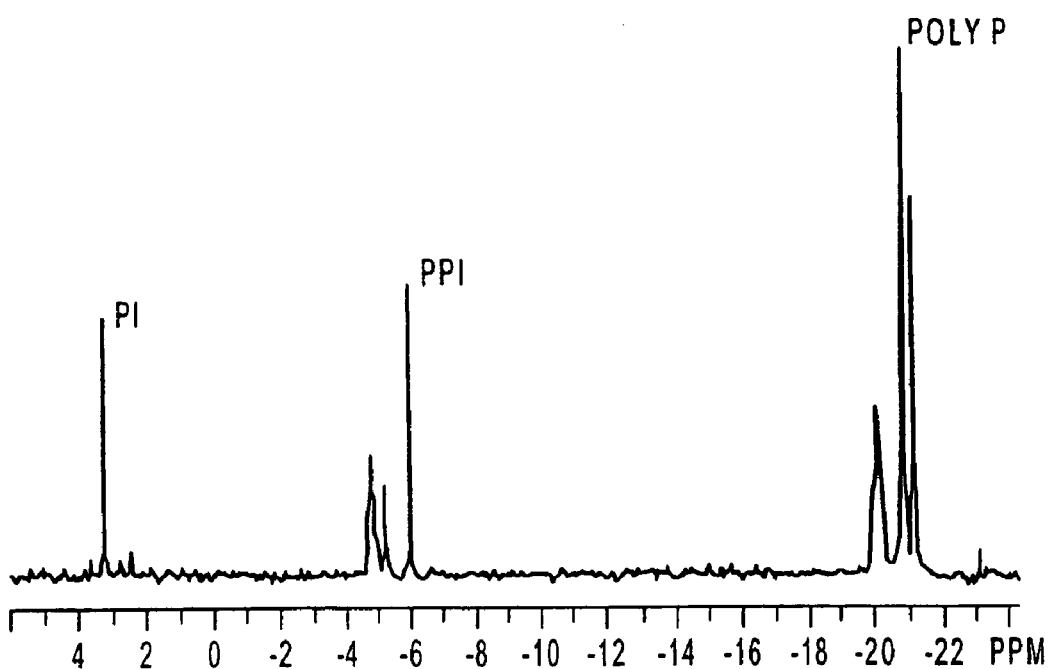
FIG. 3 is a NMR spectrum showing that the polyphosphate is the predominant form of the inorganic phosphate.
Figure 4:
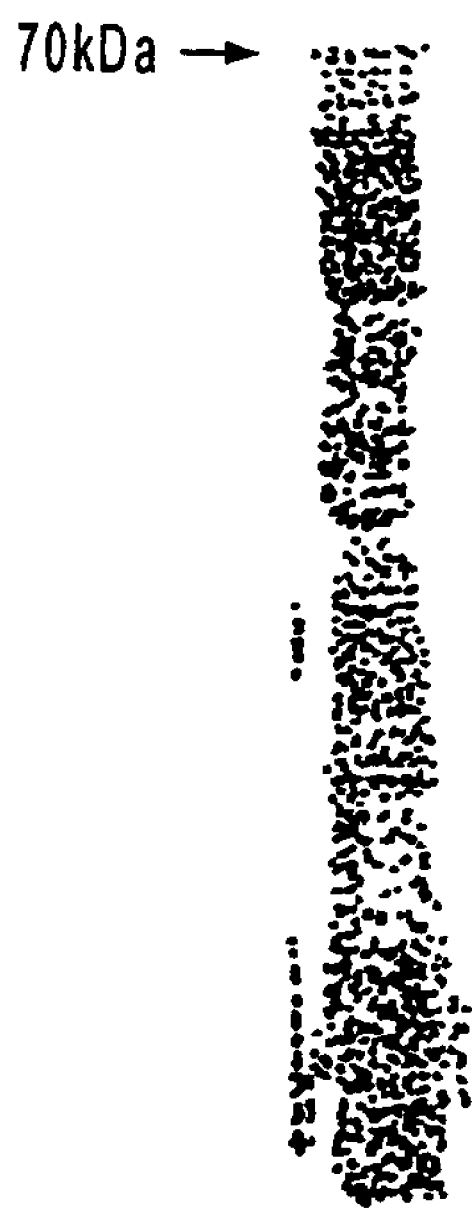
FIG. 4 is an SDS-PAGE of the detergent-insoluble pellet indicating that the major protein is a 70 kDa protein.

Strain CC-373 (ac-u-c-2-21) used in this example was a gift from a stock maintained at the *Chlamydomonas* culture collection at Duke University, Durham, N.C. Cells grown in a minimal inorganic medium at 25° C. in the light for 3 to 4 days (late log to stationary phase) were harvested by centrifugation at 1000 g. The medium was formed of the following: 7.5 mM sodium acetate, 1.0 mM sodium citrate, 3.0 mM $K_2PO_4$, 7.0 mM $KH_2PO_4$, 7.5 mM $NH_4Cl$, 0.1 mM $CaCl_2$, 1.0 mM $MgSO_4$, 0.01 mM $FeCl_3$ supplemented with 1 ml/l trace metals in the concentration of (mg/100 ml) $H_3BO_3$, 100; $ZnSO_4.7H_2O$, 100; $MnSO_4.4H_2O$, 40; $CoCl_2.6H_2O$, 20; $Na_2MoO_4.2H_2O$, 20; $CuSO_4.5H_2O$, 6. The pelleted cells were suspended in 50 mM phosphate buffer (pH 7.0) or 10 mM Tris-HCl (pH 8.0) containing 1.0% (w/v) Triton X-100, broken by sonication and centrifuged at 1000 g for 5 min. The pellet was washed two times with 1.0% Triton X-100 in buffer (50 mM phosphate, pH 7.0) and then two times with buffer. The resulting pellet contains zeaxanthin, lutein, polyphosphate, $Ca^{2+}$, $Mg^{2+}$, several proteins and starch (FIGS. 2–4). Oxygenated carotenoids can be liberated from the pellet fraction by a simple heating treatment.

Figure 1:
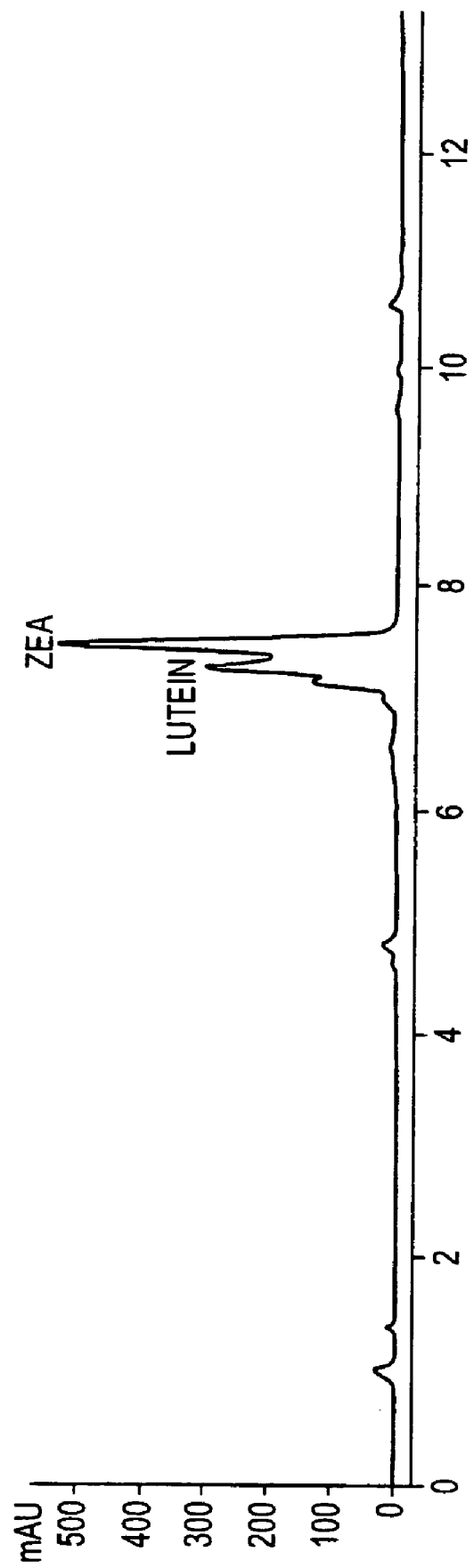
FIG. 1 is an output of a high pressure liquid chromatograph of acetone extracted pigments recovered from a detergent-insoluble pellet, during an example in accordance with the invention.

Analysis of carotenoid composition of *Chlamydomonas reinhardtii* CC-373 demonstrated that the strain was deficient in the epoxidated carotenoids neoxanthin (3S,5R,6R,3'S, 5'R,6'S)-5',6'-epoxy-6,7-didehydro-5,6,5'6'-tetrahydro-β,βcarotene-3,5,3'-triol), violaxanthin ((3S,5R,6S,3'S,5'R,6'S)-5,6,5',6'-diepoxy-5,6,5',6'-tetrahydro-β,β-carotene-3,3'-diol, and antheraxanthin ((3S,5R,6S,3'R)-5,6-epoxy-5,6-dihydro-β,β-carotene-3,3'-diol). In whole cells, the amount of zeaxanthin ((3R,3'R)-β,β-carotene-3,3'-diol) was increased to a level greater than that of lutein ((3R,3'R,6'R)-β,ε-carotene-3,3'-diol). Upon analysis, only a relatively small amount of zeaxanthin was present in the membrane, which is traditionally considered its normal physiological domain. Rather, the bulk of zeaxanthin was recovered in a Triton X-100-insoluble pellet fraction (FIG. 1). The Triton X-100-insoluble fraction pelleted through 1.5 M sucrose, a characteristic of polyphosphate granules that form within cytoplasmic vacuoles. Electron micrographs suggest that the membrane of these vacuoles is derived from the chloroplast envelope. The formation of these dense cytoplasmic vacuoles is not confined to *Chlamydomonas* but is thought to be common through Chlorophyta, i.e. *Dunaliella*, etc. The apparent transfer of zeaxanthin to chloroplast envelope-derived cytosolic vacuoles allows for the simple preparation of a zeaxanthin enriched product without the use of solvents.

The foregoing description provides an enabling disclosure of the invention, which is not limited by the description, but only by the scope of the appended claims. All those other aspects of the invention, and their equivalents, that will become apparent when a person of skill in the art has read the foregoing, are within the scope of the invention and of the claims hereinbelow.

I claim:

1. A method of producing a carotenoid in a detergent-insoluble pellet purified from soluble cellular components comprising:
   culturing a strain of Chlorophyta algae cells in a minimal inorganic growth medium;
   separating said algae cells from said minimal inorganic growth medium to obtain harvested algae;
   treating said harvested algae with detergent to obtain a detergent-insoluble pellet fraction comprising a carotenoid; and
   separating said detergent-insoluble pellet fraction from soluble cellular material.

2. The method of claim 1, wherein said strain of Chlorophyta algae cells comprises a strain of *Chlamydomonas* cells.

3. The method of claim 1, wherein the carotenoid is selected from zeaxanthin and lutein.

4. A detergent-insoluble pellet form of carotenoid, the pellet form obtained from a process comprising:
   culturing a strain of Chlorophyta algae cells in a minimal inorganic growth medium;
   separating said algae cells from said minimal inorganic growth medium to obtain harvested algae;
   treating said harvested algae with detergent to obtain a detergent-insoluble pellet fraction comprising a carotenoid wherein liquid chromatography of said pellet fraction produces acetone extracted pigments, as shown in FIG. 1; and
   separating said detergent-insoluble pellet fraction from soluble cellular material.

5. The detergent-insoluble pellet form of carotenoid of claim 4, wherein said strain of Chlorophyta algae cells comprises a strain of *Chlamydomonas* cells.

6. The detergent-insoluble pellet form of carotenoid of claim 4, wherein the carotenoid is selected from zeaxanthin and lutein.

7. A detergent-insoluble pellet form of carotenoid, the pellet form obtained from a process comprising:
   culturing a strain of Chlorophyta algae cells in a minimal inorganic growth medium;
   separating said algae cells from said minimal inorganic growth medium to obtain harvested algae;
   treating said harvested algae with detergent to obtain a detergent-insoluble pellet fraction comprising a carotenoid wherein energy dispersive x-ray analysis of said pellet fraction, having the EDAX analysis as illustrated in FIG. 2, shows phosphate with divalent calcium and magnesium cations as a predominant inorganic component; and
   separating said detergent-insoluble pellet fraction from soluble cellular material.

8. The detergent-insoluble pellet form of carotenoid of claim 7, wherein said strain of Chlorophyta algae cells comprises a strain of *Chlamydomonas* cells.

9. The detergent-insoluble pellet form of carotenoid of claim 7, wherein the carotenoid is selected from zeaxanthin and lutein.

10. A detergent-insoluble pellet form of carotenoid, the pellet form obtained from a process comprising:
    culturing a strain of Chlorophyta algae cells in a minimal inorganic growth medium;
    separating said algae cells from said minimal inorganic growth medium to obtain harvested algae;
    treating said harvested algae with detergent to obtain a detergent-insoluble pellet fraction comprising a carotenoid wherein a sodium dodecyl (lauryl) sulfate—polyacrylamide gel electrophoresis of said pellet fraction indicates a 70 kDa protein as a major protein as illustrated in FIG. 4; and
    separating said detergent-insoluble pellet fraction from soluble cellular material.

11. The detergent-insoluble pellet form of carotenoid of claim 10, wherein said strain of Chlorophyta algae cells comprises a strain of *Chlamydomonas* cells.

12. The detergent-insoluble pellet form of carotenoid of claim 10, wherein the carotenoid is selected from zeaxanthin and lutein.

* * * * *